United States Patent [19]

Urry

[11] Patent Number: 4,500,700

[45] Date of Patent: Feb. 19, 1985

[54] ELASTOMERIC COMPOSITE MATERIAL COMPRISING A POLYPENTAPEPTIDE HAVING AN AMINO ACID OF OPPOSITE CHIRALITY IN POSITION THREE

[75] Inventor: Dan W. Urry, Birmingham, Ala.

[73] Assignee: The Board of Trustees of the University of Alabama for the University of Alabama in Birmingham, Birmingham, Ala.

[21] Appl. No.: 452,801

[22] Filed: Dec. 23, 1982

Related U.S. Application Data

[63] Continuation-in-part of Ser. No. 308,091, Oct. 2, 1981, Pat. No. 4,474,851.

[51] Int. Cl.$^3$ ............................................. C08G 69/10
[52] U.S. Cl. ................................ 528/328; 204/159.14; 428/35; 428/475.5; 525/420; 528/310; 604/8
[58] Field of Search ................................ 528/328, 310

[56] References Cited

U.S. PATENT DOCUMENTS 4,132,746 1/1979 Urry et al. ...................... 528/328

Primary Examiner—Harold D. Anderson
Attorney, Agent, or Firm—Oblon, Fisher, Spivak, McClelland & Maier

[57] ABSTRACT

An elastomeric material comprising an elastomeric polypeptide, where the polypeptide comprises pentapeptide repeating units formed of amino acid residues selected from the group consisting of hydrophobic amino acid and glycine residues where the third amino acid residue of at least one repeating unit of the polypeptide has the D configuration if the remaining hydrophobic amino acids have the L configuration or the L configuration if the remaining hydrophobic amino acid residues have the D configuration and where the repeating units exist in a conformation having a $\beta$-turn. Also disclosed are elastomeric fabrics formed from the elastomeric material and composites containing it and the use of such fabrics in vascular prosthesis, as well as a method of forming such elastomeric materials.

9 Claims, 7 Drawing Figures

4,500,700

ELASTOMERIC COMPOSITE MATERIAL COMPRISING A POLYPENTAPEPTIDE HAVING AN AMINO ACID OF OPPOSITE CHIRALITY IN POSITION THREE

BACKGROUND OF THE INVENTION

This work was supported in part by the National Institutes of Health under Grants No. HL-11310 and HL-29578.

This is a continuation-in-part of application Ser. No. 308,091, filed Oct. 2, 1981 now U.S. Pat. No. 4,474,851.

1. Field of the Invention

This invention relates to elastomeric fibers, to fabrics made from such fibers that are useful in cardiovascular prosthesis, and more particularly to an elastomeric polypentapeptide comprising a D-amino acid.

2. Description of the Prior Art

Replacement of a blood vessel by a prosthetic device is an important and common practice in modern vascular surgery. Although some use is made of veins or arteries taken from other portions of a patient's body, most of such prosthetic devices are prepared from artificial materials that can be prepared in a variety of sizes and stored in a sterile state ready for use.

There are several essential properties of cardiovascular prosthetic materials, among which are the following:

1. Retardation of thrombosis and thromboembolism (antithrombogenic);
2. Minimal harm to blood cells and minimal blood cell adhesion;
3. Long life as prosthetic inserts; and
4. High compliance with the physical and chemical properties of natural blood vessel such as similar elastic modulus and tensile strength.

Another useful property would be a chemotaxis that induced rapid endothelialization and invasion of connective tissue cells for vascular wall reconstruction in a manner such that the prosthesis would be slowly replaced by and/or integrated into newly synthesized internal elastic lamina. None of the materials presently being used can fulfill all of these requirements.

The most commonly used fabric for blood vessel prosthesis is made from Dacron (Trademark, DuPont), a synthetic polyester fiber made from polyethylene terephthalate. Dacron has been used in several weaves and in combination with other materials. An example of a frequently used material is the DeBakey Elastic Dacron fabric manufactured by USCI, a division of C. R. Bard, Inc. (Cat. No. 007830). Other commonly used materials are felted polyurethane and polytetrafluoroethylene (Berkowitz et al, Surgery, 72, 221 (1972); Wagner et al, J. Surg. Res., 1, 53 (1956); Goldfarb et al, Trans. Am. Soc. Art. Int. Org., XXIII, 268 (1977)).

However, none of these materials, even when specially woven or crimped, mimics the elastic nature of natural blood vessel walls (Takabayashi et al, J. Sur. Res., 19, 209 (1975)). Because of this, blood pressure response and blood flow occur differently in natural and artificial blood vessels, and the desirable normal flow characteristics and pressure response are not attained. Changes in blood flow are undesirable and often lead to clotting. A high compliance material that more closely mimics the natural elastic behavior of blood vessels is still needed.

SUMMARY OF THE INVENTION

Accordingly, it is an object of this invention to provide an artificial material having elastic character such that a blood vessel prosthesis produced from such a material would mimic the pressure response characteristics of natural blood vessels.

It is a further object of this invention to provide an artificial material suitable for blood prosthesis having chemical properties that closely resemble the chemical properties of natural blood vessel elastic lamina.

These and other objects of this invention as will hereinafter become more readily apparent have been attained by providing an elastomeric material, comprising an elastomeric polypeptide, wherein said polypeptide comprises pentapeptide repeating units, wherein said repeating units comprise amino acid residues selected from the group consisting of hydrophobic amino acid and glycine residues wherein the third amino acid residue of at least one repeating unit of said polypeptide has the D configuration, if the remaining hydrophobic amino acid residues have the L configuration, or the L configuration, if the remaining hydrophobic amino acid residues have the D configuration, and wherein said repeating units exist in a conformation having a $\beta$-turn.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings and photomicrographs, wherein.

DESCRIPTION OF THE PREFERRED EMBODIMENTS

Figure 1:
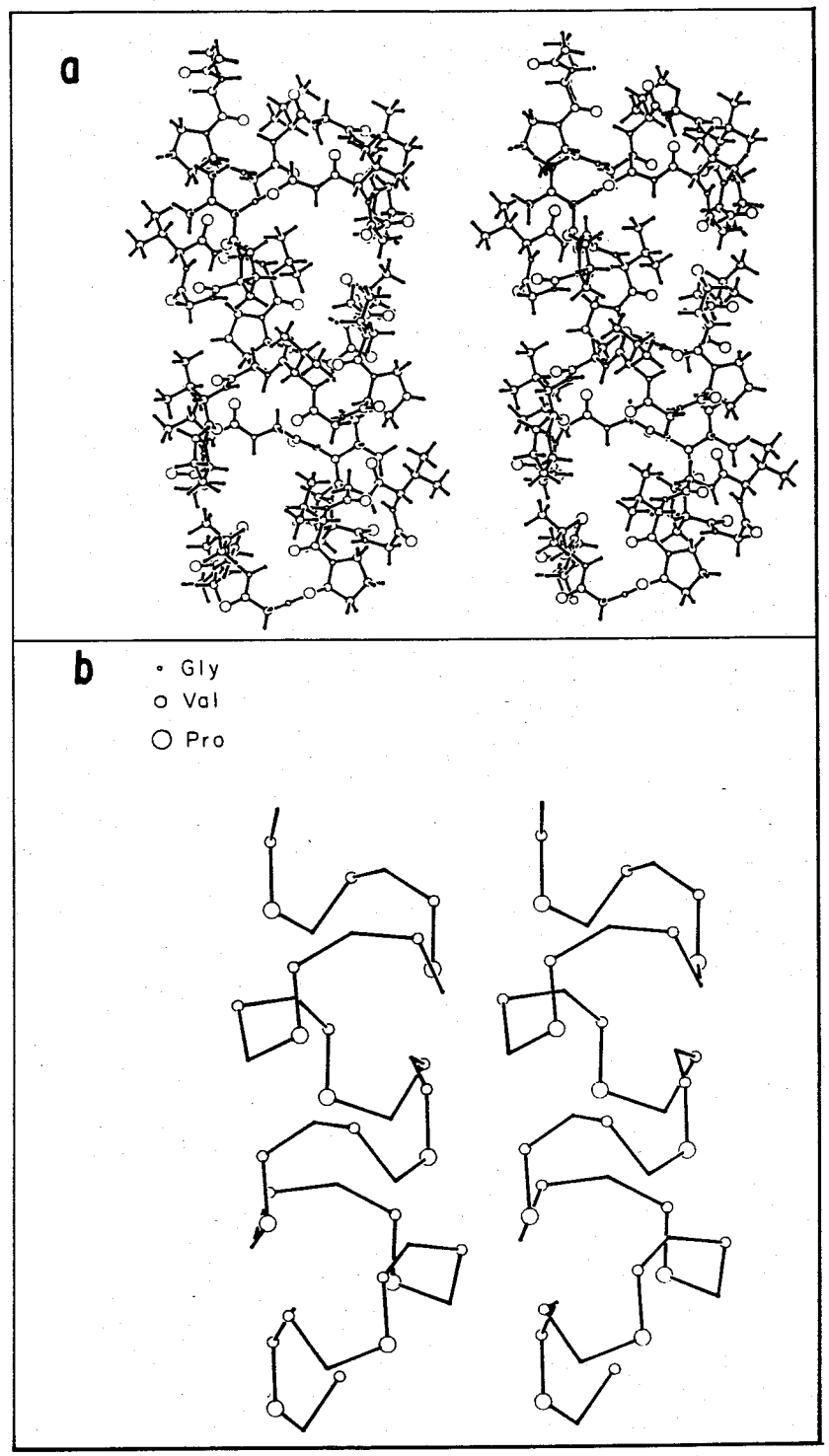
FIG. 1 shows a series of computer-generated stereoscopic drawings of a $\beta$-spiral structure of a polypentapeptide in which the third amino acid residue is an achiral glycine residue.

The present invention arose as the result of investigations into the structure of elastic fibers present in blood vessel walls and other elastic materials, such as ligaments, present in humans and animals. The connective tissue of vascular walls is formed from two principal types of protein. Collagen, the principal proteinaceous component of connective tissue, forms the strength-giving structure. In the vascular wall, and particularly in its internal elastic lamina, collagen is associated with natural elastic fibers formed from a different protein. In the relaxed wall of the collagen fibers tend to be folded or crimped, and the elastic fibers are in their retracted state. On distension or stretching, the elastic fibers stretch out, and, as their extension limit is approached, the collagen fibers come into tension to bear the load. As the load diminishes, the elastic fibers draw the wall back to its original dimensions and the collagen fibers back into their folded state. In a synthetic vascular material of the types currently available, such as Dacron, the weave can be viewed as providing the structural analogue of folded collagen, but there is no true elastomeric component.

The central portion of the elastic fibers of vascular wall, skin, lung and ligament is derived from a single protein called tropoelastin. Polypeptide sequences of tropoelastin from vascular wall have been shown by Sandberg and colleagues to contain a repeat hexapeptide (Ala-Pro-Gly-Val-Gly-Val)$_n$, a repeat pentapeptide (Val-Pro-Gly-Val-Gly)$_n$, and a repeat tetrapeptide (Val-Pro-Gly-Gly)$_n$, where Ala, Pro, Val and Gly respectively represent alanine, proline, valine and glycine amino acid residues. (Peptide representations in this application conform to the standard practice of writing the $NH_2$-terminal amino acid residue at the left of the formula and the $CO_2H$-terminal amino acid residue at the right). A high polymer of the hexapeptide has been synthesized, whereby it forms cellophane-like sheets. The hexapeptide is therefore thought to fill a structural role in the natural material. Synthetic high polymers of the pentapeptide and of the tetrapeptide, on the other hand, are elastomeric when cross-linked and appear to contribute to the functional role of the elastic fiber. For example, the chemically cross-linked polypentapeptide can, depending on its water content, exhibit the same elastic modulus as native aortic elastin.

Investigations into the structure of the natural polypentapeptide (PPP) and polytetrapeptide (PTP) have disclosed several features in common and have led to the present invention by uncovering the essential features responsible for the elasticity of these molecules. Now that these features have been discovered, it is possible to predict which other polypeptides will exhibit elasticity, thereby making possible the synthesis of a new class of elastomeric materials. Of course, it is likely that not all elastic polypeptides function in the way described herein or have the same structural features. Other modes of action responsible for elasticity are likely to exist in molecules of different structure and, if so, may have no resemblance to the elastomeric molecules described herein.

The preliminary investigations leading to the present invention were described in a prior patent application by the same inventor, Ser. No. 308,091, filed Oct. 2, 1981, which is herein incorporated by reference. An essential feature of the elastomeric PPP and PTP of the earlier invention and of the D-amino acid-containing pentapeptide of the present invention is the existence of a sequence of regularly appearing β-turns in the protein's secondary structure, i.e., the conformation of its peptide chain. A β-turn is characterized by a ten atom hydrogen bonded ring of the following formula:

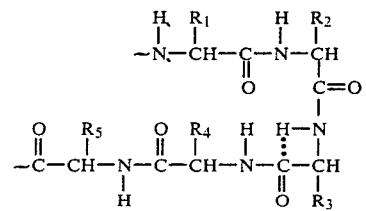

In this formula, $R_1$–$R_5$ represent the side groups of the respective amino acid residues.

Stereoscopic views of a PPP of the earlier invention are shown in FIG. 1, which shows a series of β-turns repeating in a regular sequence, one β-turn for each pentapeptide repeating unit. In these views the overall conformation of the peptide chain is a β-spiral, i.e., a series of regular repeating β-turns. The form of the β-spiral is best seen in FIG. 1B, in which the position of each amino acid is represented by a dot or circle. FIG. 1A shows the structure and conformation of each amino acid in the β-spiral by showing the position of each atom in the PPP. It can be seen from these stereoscopic views that the spiral structures are more open than the more common α-helix. As a result, the atoms between the atoms that participate in hydrogen bonding have a relatively great freedom of movement, more so than in an α-helix. This is particularly true of librational motions involving peptide moieties. A libration is a torsional oscillation involving simultaneous rotational motions of the two single bonds on each side of a librating moiety. The moiety involved in a libration may be a single peptide bond or several peptide residues. For adequate freedom of motion to exist, it is important, however, that the carbonyl oxygen and the amino hydrogen of the peptide bond not be involved in hydrogen bonding to other parts of the molecule or to other peptide molecules. Otherwise a greater energy barrier to the libration exists and motion will be restricted. Since non-hydrogen-bonded segments having freedom of motion exist in the β-spiral between the points of hydrogen bonding for the β-turns, these segments may be said to be librationally suspended. Librationally suspended segments therefore are a structural feature that exists in the PPP because of the repeating β-turns with relatively infrequent hydrogen bonding. Librationally suspended segments resulting from the β-spiral structure and other features still to be discussed are important features that are thought to give rise to elasticity, as will be further discussed.

Another factor leading to the high librational freedom of such molecules is the absence of polar interactions between the amino acid residues, either intrachain or interchain, other than the previously mentioned hydrogen bond. The amino acid residues present are generally all hydrophobic or glycine and accordingly do not exert significant forces on one another through space. If charged or polar groups were present, electrostatic interactions would limit librational freedom and restrict the number of available states in the relaxed (non-extended) form of the molecules. Polar and charged amino acid residues are not strictly prohibited, however, if their presence does not destroy the elasticity of the polypeptide molecule as a whole. For example, an occasional serine residue is present in the polypentapeptide sequence of naturally occurring porcine tropoelastin without destroying elasticity. Accordingly, hydrophobic amino acid residues and glycine are preferred in forming elastomeric polypeptides of the present type although other amino acids may be present to a small extent.

The size of the repeating unit is important in determining the stability and dynamic properties of the $\beta$-spiral. Repeating units having fewer than four or more than five amino acid residues do not easily form $\beta$-spirals having the required librational motions. Three amino acid residues are too few for an efficient $\beta$-turn and six residues can result in intervening segments so long that other conformations become energetically more stable. Thus, elastomers of the present type appear to be limited to polypeptides having tetrapeptide or pentapeptide repeating units. Specifically, elastomers containing an amino acid residue of opposite chirality at position three are now believed to be limited to polypentapeptides or polytetrapeptides, with polypentapeptides being particularly important.

When a peptide sequence has been identified in connection with a particular biological function such as elasticity, it is reasonable to assume that this elastomer has properties which are near optimal for its specific function. It can generally be assumed that the long period of evolution has optimized the structure of the natural biological material for its function. However, this can of course be true only to the extent that the building blocks are accessible to the evolving organisms. Proteins derived by means of the genetic code, for example, can only contain L-amino acid or glycine residues. This means that replacement of a glycine residue by a D-amino acid, even if it were to result in a functionally improved material, would not be possible for the evolving organism. The present invention has arisen as a result of selective replacement of glycine residues in the repeating units of the pentapeptide with hydrophobic D-residues. Studies of the dominant conformational feature of the polypentapeptide of elastin, the II Pro$_2$-Gly$_3$ $\beta$-turn previously discussed, indicates that a D-residue at position three will stabilize the $\beta$-turn. It has now been discovered that substituting a D-amino acid residue for the Gly$_3$ residue produces an elastomeric molecule (after cross-linking) having an elastic (Young's) modulus approximately twice that obtained for the corresponding molecule having a Gly$_3$ residue.

It is preferred that the amino acid residue in position three be a hydrophobic D-amino acid although other D-amino acids are also contemplated to be within the scope of the present invention. Amino acid residues having no more than 10 carbon atoms in their amino acid side chain are preferred. Preferred hydrophobic side chains are alkyl, aryl, and arylalkl, where aryl represents a phenyl or alkyl-substituted phenyl group. Particularly preferred are the residues of D-alanine, D-valine, D-leucine, D-isoleucine, D-phenylalanine, D-2-aminobutanoic acid, and other molecules of similar size, polarity, and chirality. Especially preferred are alkyl side chains having 1–4 carbon atoms in an $\alpha$-amino acid residue having an $\alpha$-hydrogen.

The choice of individual amino acids from which to synthesize the remaining sections of the repeating units and resulting polypeptide is unrestricted so long as the resulting structure comprises librationally suspended segments in a $\beta$-spiral. The amino acids are not restricted to $\alpha$-amino acids, although these are preferred, since it has recently become possible to predict the occurrence of $\beta$-turns from the $\alpha$-amino acid sequence of a polypeptide. A review article discussing the prediction of protein conformation, including the prediction of $\beta$-turns, was recently published by Chou and Fasman, Ann. Rev. Biochem., 47, 251 (1978), which is herein incorporated by reference. The size of the side chains present in the hydrophobic amino acids does not greatly affect the $\beta$-spiral since the side chains generally extend outward from the surface of the helix with some important but non-restrictive interturn hydrophobic interactions. However, in order to minimize interchain interactions, it is preferred that the side chain contain no more than 10 carbon atoms. Preferred hydrophobic side chains are the same as those previously described for position three, except that the resulting amino acid residues are of the opposite chirality. In addition, it appears from the studies leading to the present invention that preferred side chains of the amino acids are hydrogen or hydrocarbon chains having 1–4 carbon atoms. Examples of especially preferred residues are glycine and the naturally occuring L-amino acids alanine, valine, leucine, and isoleucine as well as closely related molecules such as 2-methyl-2-aminopropanoic acid, L-2-aminobutanoic acid, and L-2-methyl-2-aminobutanoic acid, although it is preferred that the $\alpha$-carbon have an $\alpha$-hydrogen. Proline is also a preferred amino acid.

Given positions of the repeating units have amino acid residues that are particularly preferred. The first amino acid residue is preferred to be valine, leucine, or isoleucine; the second is preferred to be proline; the third has been previously discussed; the fourth is preferred to be valine, leucine or isoleucine; and the fifth residue is preferred to be glycine. A particularly preferred repeating unit is L-Val-L-Pro-D-Ala-L-Val-Gly.

An elastomeric polypeptide consisting entirely of repeating units in which the third amino acid residue is of opposite chivality, as described herein, has an elastic modulus approximately twice that of an otherwise identical polypeptide in which all the amino acids have the same chivality, such as those described in U.S. Pat. No. 4,187,852 to the same inventor. Accordingly, it is possible to easily control the elastic modulus by using a mixture of monomers of the two types. Elastomers having at least one repeating unit in which the third amino acid is of opposite chivality are contemplated to be within the scope of the present invention.

Although applicant does not wish to be bound or limited to the following theory, it appears that the elasticity of polypeptides of the structure discussed above is caused by thermodynamic drive toward greater entropy. The relaxed state of the $\beta$-spiral has a large degree of librational freedom and thus the atoms of the peptide chain can exist in a large number of positions. When the molecules are stretched, the degree of freedom is reduced, particularly for librational motions, and when the tension is released, a thermodynamic driving force toward higher entropy results in reformation of the contracted $\beta$-spiral.

A major limitation of the previously disclosed polytetrapeptide and polypentapeptide having glycine units at position three is that relatively large cracks, which are visible under the scanning electron microscope, occured during drying of these materials. On the other hand, the D$_3$ analogues are most commonly characterized by the absence of cracking and, when cracking does occur, only smaller cracks appear and then only in limited regions. This suggests that D$_3$ analogues possess greater strength and cohesiveness in the coacervated state, properties which enhance the usefulness of these materials in prosthetic devices.

Because of the chirality of amino acids and of polypeptides produced therefrom, an equally effective polypeptide can be produced by using polypentapeptide repeating units in which all of the amino acids having chiral centers are of the opposite chirality from that previously described; i.e., the residue at position three is an L-amino acid and the remaining residues are D-amino acids or glycine. Since both L- and D-amino acids are available commercially and can be used as starting materials in a synthesis of the polypeptide of the invention, for example in the method disclosed later, either of these species of the invention may be easily produced. However, since D-amino acids are relatively more expensive, the more preferred species is that in which most of the amino acid residues are derived from L-amino acids and only the residue at position 3 is derived from a D-amino acid. Accordingly, the remainder of this disclosure will discuss only predominantly L-amino acid-containing polypeptides since those skilled in the art will recognize that predominantly D-amino acid-containing species can be easily produced in a like manner by a proper selection of amino acid starting materials.

It should be noted that not every amino acid residue in the polypeptide may be replaced by an amino acid of the opposite chirality. Random replacement leads to destruction of the $\beta$-turn and loss of elastic modulus. For example, replacement of an $\alpha$-hydrogen of the Gly$_5$ residue by a methyl moiety, i.e., synthesis of the L.Ala$_5$ PPP, was carried out as a specific test of the proposed librational freedom mechanism of elasticity. The elastomeric properties in the resulting material were entirely lost even though the $\beta$-turn, while weakened, was still present. Likewise, synthesis of a D.Ala$_5$ analog resulted in a material which did not resist the stress of drying. Scanning electron micrographs of a D.Ala$_5$ PPP-Dacron fiber composite showed that the elastomeric matrix ruptures during the stresses of drying and of stretching while wet. Thus, the effect of adding a methyl moiety to the Gly$_5$ residue of the polypentapeptide is to decrease markedly the mobility of the polypeptide chain and to destroy elasticity. Based on structural studies of the $\beta$-turn model, it presently appears that only pentapeptides of the invention having the third residue of opposite chirality will retain sufficient librational mobility in a $\beta$-turn to produce elasticity according to the mechanism proposed herein.

A second major limitation of the polypentapeptide even when cross-linked, is that, while elastomeric, this material is somewhat lacking in strength. The limited strength of the synthetic matrices is not unlike the biological situation, as the role of the elastic fibers is not one of load bearing but rather of providing resistance to extension, and of reforming the original tissue configuration when tension is released. Thus an improved prosthetic material can be produced by using a collagen-like load bearing component in addition to an elastomeric component of the correct elastic modulus. This can be achieved by compounding the synthetic elastomeric high polymers described above to a second material with greater strength. The second material forms the core of the composite fiber and will be referred to as the "collagen analogue" or "core fiber". The term core fiber is not limited to those forms of elastomeric composite materials in which a first fiber is coated with a second material, but also refers to other forms in which a strength giving fiber (the core fiber) is chemically bonded to a second component that is elastomeric (the polypeptide). For example, elastomeric polypeptide fibers may form strands between the segments of a crimped core fiber. The essential feature is that a chemical bond (of any type) exists between the surface of the core fiber and the elastomeric polypeptide so that the two components do not become separated while the elastomeric component is being stretched or is reforming the relaxed $\beta$-spiral. The chemical bond may be covalent or ionic bonding, hydrogen bonding, or the result of electrostatic interactions of various types, such as ion-dipole and diopole-dipole interactions. Covalent bonding is preferred. Linkages may be formed in any conventional manner and, if covalent bonds are to be formed, they can be accomplished by reacting a functional group of the polypeptide with a functional group of the core fiber. The functional groups may be present naturally as part of the polypeptide or core fiber or may be formed later, for example, by suitable chemical reactions involving the already formed core fiber or polypeptide. Such chemical reactions are well known and are discussed in more detail later in connection with cross-linking of the polypeptide.

The collagen analogue may be any fiber-forming natural or artificial material having a tensile strength of 10 to 50 kg/mm$^2$, preferably about 20 to 40 kg/mm$^2$, and most preferably about 30 kg/mm$^2$ and an elastic modulus of no more than $5 \times 10^{10}$ dynes/cm$^2$, that is biologically compatible with use in a living organism. By biologically compatible is meant that the core polymer, when compounded into the final product with the elastomer, will not harm the organism in which it is implanted to such a degree that implantation is as harmful as or more harmful than the needed vascular replacement. The term artifical fiber as used herein refers both to fibers formed from synthetic materials and to fibers formed from naturally occuring materials. The term artificial refers to the act of forming the fiber rather than the act of forming the material out of which the fiber is made. If used outside the living body of an organism is anticipated, biological compatibility is not required. Examples of suitable types of polymers which can form fibers of the required properties include polyamides, polyesters, polyvinyls, polyethylenes, polyurethanes, polyethers, and polyimides. Natural fibers include collagen, which is preferred. Non-polymeric fibers, such as metal fibers, and inorganic fibers, such as glass and carbon, may be of use in some applications, although their use is less preferred.

Suitable polyamides include polyamino acids, such as poly condensation products of p-aminobenzoic acid, and condensation products of diamines with dicarboxylic acids, such as hexamethylenediamine and terephthalic acids. Another suitable polyamide would be direct synthesis of an artificial fiber modeled after natural collagen. Polyesters suitable for use with the invention include poly(hydroxy acids) and condensation products of diols or polyols with dicarboxylic acids, such as ethylene glycol and an aromatic dicarboxylic acid. Examples of polyvinyls include poly(methyl methacrylate) and other esters of acrylic and methacrylic acid, polyvinyl alcohol, and esters of polyvinyl alcohol. Polyethylenes include polyethylene itself and halogenated derivatives of polyethylenes, such as polyvinyl chloride, as well as perhalogenated polyethylene, such as polytetrafluoroethylene. Polyurethanes include addition products of aromatic, aliphatic, or araliphatic diisocyanates with either diamines or diols. Polyethers include epoxy resins such as poly(propylenoxide) and poly(ethylene oxide). Polyimides include polymers derived from pyromellitic dianhydride and aromatic or aliphatic diamines.

Preferred collagen analogues are polyesters. Preferred polyesters are condensations products of phthalic, isophthalic, or terephthalic acid and diols, of which the most preferred are polymers derived from terephthalic acid and a 1,2-diol, such as, for example, the condensation product of terephthalic acid and ethylene glycol that is sold under the trademark of Dacron by E. I. du Pont de Nemours and Co. Polyesters having aromatic nuclei, such as Dacron, can be easily derivatized in order to provide function groups for covalent attachment of the polypeptide. For example, formylation and carboxylation of aromatic rings are easily carried out, well known reactions and provide functional groups that will react with amino groups present in the polypeptide.

The polymers listed above or other suitable materials are synthesized according to standard techniques and formed into fibers or fabrics, or are obtained from commercial sources as fibers or fabrics or in a form that may be manufactured into fibers or fabrics. Methods of preparing such fibers are well known and are not considered to be part of the present invention. The list given above is not intended to be limiting and any fiber or fabric that meets the standards of strength and biocompatability previously given may be used, whether known at the time of this application or discovered later. A crimping of the core fiber that will provide a uniform extendability of 200% or more is desirable. If the fiber is formed into a fabric, this crimping may be accomplished by the fabric weaving process. Crimping and expandable weaves are well known and are not considered to be part of the essence of the invention.

The diameter of the core fiber is not limited and may be varied as needed for the intended application. When the fiber is to be used in the formation of a vascular prosthesis, a diameter of less than 20 $\mu$m will give satisfactory results. Fibers with finer diameters will have a greater surface area per unit weight and are therefore preferred in order to allow better attachment of the elastomeric material to the surface of the collagen analogue (core fiber) and a more effective refolding of the collagen analogue. Diameters of less than 2 $\mu$m are preferred with a diameter of about 1 $\mu$m being most preferred.

Synthesis of the polypeptide elastomers is straightforward and easily accomplished by a protein chemist. The resulting polypeptides have the structure X-(repeating unit)$_n$-Y where X and Y represent any chemically compatible end group on the amino and carboxyl ends of the molecule, respectively, and n is an integer equal to or greater than 40. Particularly preferred are polypeptides having molecular weights greater than 10,000 daltons. It is possible that one or more amino acid residue or segment of amino acid residues may be interspersed within the polypeptide chain so long as the elasticity of the resulting molecule is not completely disrupted.

Examples of terminal X and Y end groups include the repeating peptide units themselves with free amino or carboxylic acid groups or salts thereof and peptide or amino acid units that have retained a blocking group that was present during synthesis of the polypeptide or that have a blocking group added after formation of the polypeptide. Examples of blocking groups include t-butyloxycarbonyl, formyl, and acetyl for the amino end of the molecule and esters, such as methyl esters, as well as amides, such as the amides of ammonia and methyl amine, for the acid end of the molecule. The end groups are not critical and can be any organic or inorganic group that does not destroy the $\beta$-turn conformation of the polypeptide or confer bio-incompatibility to the molecule as a whole.

Methods of preparing polypentapeptide polymers in which the third position is occupied by a glycine residue have been disclosed in Rapaka and Urry, Int. J. Peptide Protein Res., 11, 97 (1978), Urry et al, Biochemistry, 13, 609 (1974), and Urry et al, J. Mol. Biol., 96, 101 (1975), which are herein incorporated by reference. The synthesis of these peptides is straightforward and can be easily modified to allow production of a polymer having a $D_3$ residue. The following summary, which is not to be considered limiting, is an example of one general method of synthesizing the polypeptides.

The first step in the formation of the polypentapeptide of the invention usually is synthesis of a pentapeptide monomer. Any of the classical methods of producing peptide molecules may be used in synthesizing the building blocks of the polymers of the present invention. For example, synthesis can be carried out by classical solution techniques starting from the C-terminal amino acid as a benzyl ester p-tosylate. Each successive amino acid is then coupled to the growing peptide chain by means of its water-soluble carbodiimide and 1-hydroxybenzotriazole. A typically used carbodiimide is 1-(3-dimethylaminylpropyl)-3-ethylcarbodiimide hydrochloride (EDCI). During the coupling reaction the amino group is protected. The protecting group is then removed after condensation has taken place. A suitable protecting group is tert-butyloxycarbonyl (Boc), which can easily be removed by trifluoroacetic acid.

The first product obtained in the synthesis of the pentapeptide monomer is a protected peptapeptide, such as, Boc-L-Val-L-Pro-D-Ala-L-Val-Gly-OBzl. This protected monomer is converted into the reactive monomer by, for example, removal of the Boc protecting group and replacement of the benzyl ester with the p-nitrophenyl ester, for example by exchange with p-nitrophenyl trifluoroacetate. The resulting reactive monomer is polymerized, in the presence of a catalyst such as triethylamine if necessary, to give the polypeptide. A blocking group, such as H-Val-OMe may be added at the conclusion of the polymerization reaction to convert the remaining reactive p-nitrophenyl esters to non-reactive terminal groups if desired.

When a modified chemical structure is desired, as, for example, when chemical cross-linking will be carried out, side-group-blocked lysine or glutamic acid (or another amino acid with a protected side group capable of forming a cross-link after the protecting group is removed) may be utilized in place of one of the normal amino acids that is present in the polypeptide chain. A synthesis of a chemically cross-linked polypentapeptide having a Gly$_3$ residue is disclosed in U.S. Pat. No. 4,187,852, which is herein incorporated by reference.

If the $D_3$ polypentapeptide is to be compounded into a composite fiber, the weight ratio of the core fiber to the sheath component can vary as required for the intended use, with a ratio of from 10:1 to 1:10 being preferred, with from 1:1 to 3:10 being most preferred, when the composite fiber is to be used in a prothesis for a major artery. Lesser amounts of the elastomeric component, preferably about a 1:1 ratio, is preferred for a small artery prosthesis.

The two components are brought together in any manner that results in the formation of a synthetic composite fiber in which the high strength polymeric fiber forms a core which is surrounded by a sheath of the polypeptide. It is desirable to have the elastomeric component bridge between folds in the collagen analogue. In general, this can be accomplished by coating a preformed, crimped polymeric fiber or woven fabric with a solution, suspension, or coacervate of the polypeptide, although it may be possible to spin or otherwise form the core fiber in a solution or suspension of the polypeptide.

A preferred method of forming the composite takes advantage of the property of coacervation exhibited by the $D_3$ polypentapeptide ($D_3$-PPP). The $D_3$-PPP is soluble in water at temperatures below 20° C. but on raising the temperature above 20° C. the polymers associate and settle to form a dense, sticky phase called the coacervate. The process is entirely reversible, though dissolution can be slow. In order to impregnate the collagen analogue in preparation for compounding, fibers or strips of fabric made from the collagen analogue can be placed on the bottom of a chamber of like dimension. It is preferred to use a polytetrafluoroethylene chamber since the coacervates do not adhere well to polytetrafluoroethylene. Aqueous solutions containing $D_3$ PPP are added to each chamber covering the fabric. The temperature is raised and the coacervate allowed to settle onto the surface of the fiber or into the weave of the fabric. If a fabric is used, it is preferred to largely fill the spaces between the fibers of the fabric. The supernatant can be either removed or allowed to dry down to the level of the fabric strip. The $D_3$-PPP impregnated strip or fibers are then removed from the chambers.

Other examples of methods of depositing the polypeptide on the surface of the core fiber include evaporation of solutions of the polypeptide on the surface of the fiber and reacting the polypeptide with functional groups present in the core fiber while the core fiber is suspended in a solution of the polypeptide.

It is generally desirable to cross-link the molecules of the polypeptide in order to increase its strength and elasticity. If a composite fiber is being formed, it is preferred to perform the cross-linking after the polypeptide has adhered to the core fiber. The method of creating the linkage is not limited to the methods disclosed in this application and may be any method of covalent or non-covalent linkage that does not prevent the $D_3$ PPP or the composite fiber from behaving as an elastomer. Suitable methods and types of linkages include cross-linking with ionizing irradiation and chemical modification or substitution of amino acid residues of the peptide repeating units and of the collagen analogue repeating units in order to form reactive side groups that undergo chemical reaction with each other (chemical cross-linking) e.g., by amide linkage, aldol condensation, Schiff base formation, enzymatic cross-linking by lysyloxidase, or ester formation. Another suitable method of cross-linking comprises the use of photoactivated agents such as those giving rise to carbenes or nitrenes which may be attached as amino acid side groups or introduced as separate diffusible molecules.

A preferred type of chemical cross-linking occurs when polypeptides are prepared in which some of the repeating units are replaced by units in which one of the amino acid residues is replaced by the residue of an amino acid that has a reactive side chain. Preferred is preparation of a first batch of polypeptide in which a residue of some of the repeating units is replaced by an amino acid dicarboxylic acid, such as aspartic or glutamic acid, and a second batch of polypeptide in which a residue of some of the repeating units is replaced by a diamino carboxylic acid, such as lysine or ornithine. After a mixture of these two batches has been formed into a sheath around the core fiber, the free amino and carboxylic acid side group are allowed to react to create the cross-linkages. Formation of cross-linked PPP produced in this manner is described in U.S. Pat. No. 4,187,852, which is herein incorporated by reference. If chemical cross-linking is used, it is also necessary to provide reactive functional group in the core fiber so that linkages between the peptide elastomer and the core fiber will also occur. Such modifications are well understood by polymer chemists and may include, for example, glycidyl esters of acrylates or methacrylates (as examples of reactive groups present during formation of the core polymer), or amino or carboxylic acid groups added to the terephthalic acid moeity of Dacron (as examples of reactive groups formed after formation of the core fiber).

The degree of cross-linking is such that elastomeric properties are imparted to the resulting composite fiber and can be varied to provide the desired dynamic mechanical properties. Preferred is an average of one cross-link for every 10 to 100 pentamer repeating units with 20 to 50 being most preferred. The degree of chemical cross-linking can be controlled by selecting the proper proportions of reagents. In general, the ratio of repeating units with reactive side groups to unmodified repeating units within a single molecule can vary from 1:1 to 1:20 with a ratio of about 1:5 being preferred. When two batches of polypeptide containing carboxylate or amino side groups as described above are used, the ratio of carboxylate-side-group-containing polypeptide to amino-side-group-containing polypeptide can vary from 4:1 to 1:4 with a ratio of about 1:1 being preferred.

When irradiation cross-linking is performed, a satisfactory approach is irradiation with gamma radiation from a cobalt-60 source. Other radiation energies required to provide a cross-linking action without excessive destruction of the core fiber or elastomeric peptide structure may be easily determined by simple experimentation. The degree of cross-linking is determined by the length of time and energy of the irradiation when irradiation cross-linking is performed. At least two cross-linkages per molecule are needed. The number of cross-linkages per molecule and the elastic modulus increase as the radiation dose increases. The requisite time for any desired amount of cross-linking is easily determined by simple experimentation for any given source of irradiation energy. Samples of non-cross-linked polymer or composite fiber are exposed to the source of ionizing energy for varying lengths of time, and the resulting elastic modulus is measured. In this manner the irradiation time required to produce an elastic modulus necessary to match a specific design characteristic of the polymer or composite fiber can easily be determined. For use in forming vascular wall prosthetic devices, an elastic (Young's) modulus of $10^6$ to $10^7$ dynes cm$^2$, preferably about $4 \times 10^6$ dynes/cm$^2$, for the cross-linked composite fiber is desired. This is approximately the elastic modulus of the vascular wall.

The elastomeric composite fibers may be woven into a fabric or an elastomeric fabric may be formed from a fabric of the core fiber material by coating and cross-linking the polypeptide on the surface of the fibers of the preformed fabric. When the resulting fabric has an elastic modulus of from $10^6$ to $10^7$ dynes/cm$^2$ and has been formed into an appropriate shape, for example, a tubular shape, the resulting article may be used in vascular prosthesis. One simple way to obtain the desired tubular form, not considered to be limiting, would be to place the preformed woven and crimped tube of core fiber material between two concentric glass tubes with the outer tube containing an aqueous solution of D$_3$-PPP. The temperature of the solution would then be raised to allow coacervation to take place and the resulting impregnated woven fabric composition would be cross-linked by γ-irradiation at an appropriate dose.

It is also possible to form separate strength-giving and elastomeric fibers and to interweave them into a fabric of the desired shape. The first fiber, which is essentially non-elastic, would provide strength while the elastomeric polypeptide fiber would provide elasticity.

Once the synthetic composite material has been formed into an appropriate shape, if it is intended for use as a vascular replacement or patch, it is surgically inserted into a human or animal in place of diseased or missing vascular material. Tubular material may be used to replace an entire vein or artery by attaching each end to the distal and proximal free ends of a blood vessel having a missing or surgically removed section. Attachment is made so that blood flows through the tube without major leaking by any means capable of providing medically acceptable attachment, such as suturing or cauterizing. The elastomeric composite may be made in the form of a patch to be attached by the same methods if replacement of only a portion of a blood vessel is desired. Also tubular material may be used as a lining to replace diseased termica intima following endarterectomy.

Other uses of the elastomic material of this invention are also contemplated. The elastomer itself or the composite elastomeric fiber can be formed into sutures or used in the formation of artificial ligaments. As was previously described, the elastic modulus is easily controlled, resulting in a material having broad use, both in biological systems for replacement and repair of natural parts of an organism and in the myriad of nonbiological uses presently fulfilled by other elastomers.

The above disclosure generally describes the present invention. A more complete understanding can be obtained by reference to the following specific examples, which are provided herein for purposes of illustration only and are not intended to be limiting unless otherwise specified.

Example: Synthesis and Characterization of a D$_3$ Polypentapeptide

Methods and Materials

Synthesis: The synthesis of the peptide, Boc-Val-L-Pro-D-Ala-L-Val-Gly-OBzl (I), was carried out using classical solution methods starting from the C-terminal glycine benzyl ester p-tosylate. Each amino acid was coupled to the growing peptide chain by means of the water soluble carbodiimide 1-(3-dimethylaminopropyl)-3-ethylcarbodiimide hydrochloride (EDCI) and 1-hydroxybenzotriazole. The tert-butyloxycarbonyl group was used for amino group protection, and its removal was achieved with trifluoroacetic acid. Peptide I was converted to the free acid by hydrogenolysis and then to the corresponding p-nitrophenyl ester using p-nitrophenyl trifluoroacetate. After deblocking the N$^\alpha$-protecting group and neutralizing, H-L-Val-L-Pro-D-Ala-L-Val-Gly-ONp was polymerized in dimethyl sulfoxide for 14 days. The reaction mixture was diluted with water, dialyzed against water and lyophilized. Purity of all intermediate peptides was checked by thin layer chromatography and C-13 NMR spectra. The overall yields were 80–90% in the preparation of the intermediate products and 50% during the polymerization step.

Nuclear Magnetic Resonance: A JEOL FX-100 NMR spectrometer equipped with a 5 mm probe operating at 100 MHz was used to collect the proton temperature dependent data in Me$_2$SO-$^2$H$_6$. Probe temperatures were regulated by a JEOL VT-3B controller to ±2° C. and were measured using an ethylene glycol temperature standard before and after each data accumulation. Tetramethylsilane was used as the internal standard at 0 ppm.

Proton and carbon-13 assigments of the polypeptide in Me$_2$SO-$^2$H$_6$ were confirmed by heteronuclear multiple irradiation techniques as previously described in Khaled et al, J. Magn. Resonance, 44, 255 (1981). The FX-100 spectrometer was also utilized for this purpose, equipped with a multinuclear probe and a Model 1-MI multi-irradiation accessory. All of the selective decoupling experiments were performed at 70° C.

A JEOL PFT-100 NMR spectrometer operating at 25 MHz for carbon-13 was used to obtain the Me$_2$SO-$^2$H$_6$-$^2$H$_2$O solvent dependence of peptide C—O chemical shifts. Probe temperatures were maintained at 30° C., and dioxane was used as the internal standard at 67.4 ppm from an external hexamethyldisiloxane reference.

Turbidity Studies: A Cary 14 ultraviolet spectrophotometer was used to obtain the temperature profiles of turbidity formation (TPτ's). The optical densities of the sample solutions in a 1 mm cell were monitored at 300 nm during a slow, controlled heating (30°/hour). A Fluke digital voltmeter with a home-built temperature probe was used to monitor the sample temperature.

Scanning Electron Microscopy of Coacervate: For characterization of the D-Ala$_3$ PPP, coacervate from a 16 mg/ml aqueous solution was formed on a 0.8 mm thick Plexiglass substrate at 40° C. Secondary electron image micrographs of the coacervate coated Plexiglass substrate were obtained using a JEOL JSM U3 scanning electron microscope operating at 15 kV, 200μ final aperture, and a tilt of 38.5°. Specimen preparation prior to SEM examination included attachment to carbon stubs, vacuum drying, and at less than $5 \times 10^{-5}$ mm Hg coating with carbon then approximately 200 Å of Au-Pd in a JEOL JEE-4C vacuum evaporator.

Irradiation Cross-linking: Coacervation of the peptide for irradiation cross-linking was accomplished by adding 75 mg of D-Ala$_3$ PPP in aqueous solution to Debakey Elastic Dacron Fabric (USCI, a division of C. R. Bard, Inc., Cat. No. 007830) strips (7 mm×25 mm) placed in the bottom of Teflon chambers as described in Urry et al, J. Biomed. Mater. Res., 16, 11 (1982), which is herein incorporated by reference. Chamber dimensions were 4.75 mm×12.6 mm. At a slightly elevated temperature (45° C.), the coacervate settled, impregnating the Dacron knit fibers. The impregnated Dacron strips were removed, sealed in 2.5 cm×2.5 cm glass slides containing a 0.24 cm thick Teflon spacer and irradiated. Gamma irradiation cross-linking was performed at the Auburn University Nuclear Science Center Facility as described in the last cited reference. Twenty-four cobalt sources, each ten inches long, three-fourths inch wide and one-eighth inch thick, were positioned in three concentric circles of four, six and eight inches diameter. Eight sources were equally spaced on the circumference of each circle. The radiation intensity was measured to be 13,317 roentgen per minute. The samples were placed in the center of the source configuration for various times so that the radiation absorbed dosages (RADs) could be varied from 1 to $100 \times 10^6$. Low dosages within this range are used with longer chain lengths of polypeptides and high dosages with shorter chain lengths. Exposure of the D·Ala$_3$ PPP impregnated Dacron to the twenty-four concentrically arranged cobalt sources was typically carried out for the appropriate time to achieve a 30 Mrad dose.

Stress-strain Characterization: Stress-strain data was recorded using an apparatus designed and built in this laboratory as described in the last cited reference. A rigidly mounted Statham model UC-2 transducing cell with UL4-0.5 load cell accessory was used to record force data. Using the required excitation and signal conditioning circuits the output of the UC-2 transducer was recorded on the y-axis of an x-y recorder. The sample was elongated at a constant rate of 2 mm/minute using a Velmex model B2509CJ Unislide driven by a variable speed motor through a Metron Instruments speed reducer. The position of the moving holder was recorded on the x-axis of the x-y recorder using a BLH linear displacement transducer and appropriate excitation and signal conditioning circuits. The thickness and the width of the sample were measured before being placed in the clamps. One clamp was attached to the UC-2 transducer and the other to the moving platform. Initial lengths ($L_i$) of 0.5 and 1.0 cm were used. The x-axis scale is $\Delta L/L_i$ where $\Delta L$ is the displacement of the moving end of the sample from $L_i$. The cross-section area was used to calculate dynes/cm$^2$ from the recorded force; i.e., Young's modulus was calculated using the cross-sectional area and force data. A constant rate of elongation (2 mm/min) was used and extensions of 40, 60, 80 and 100 percent were recorded.

RESULTS

Figure 2:
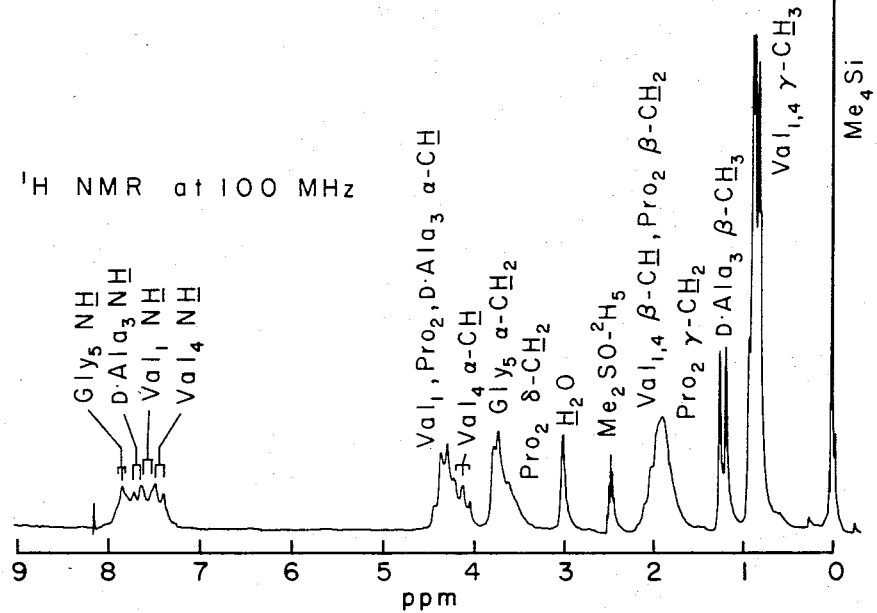
FIG. 2 shows nuclear magnetic resonance spectra in $Me_2SO$-$^2H_6$ of the D.Ala$_3$ polypentapeptide: A-100 MHz proton spectrum at 85° C., B-25 MHz carbon-13 spectrum at 30° C.
Figure 2:
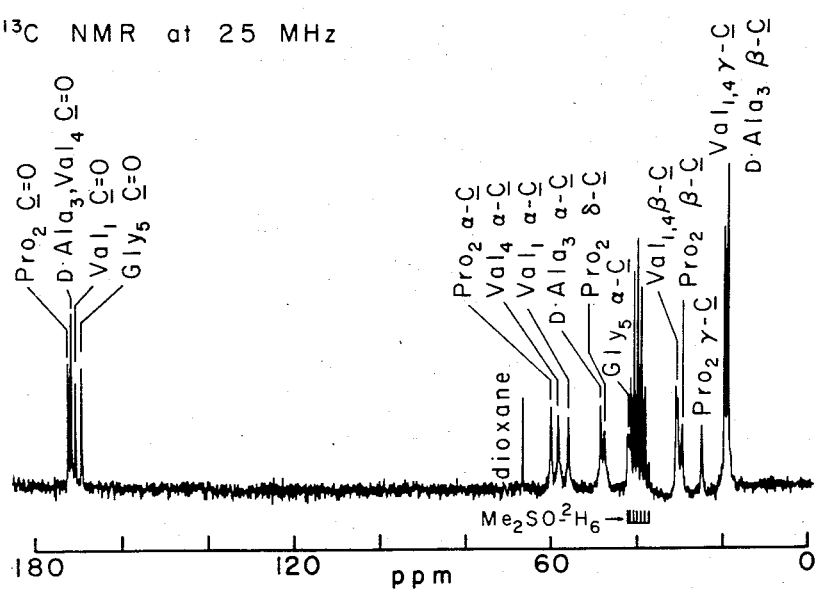

Nuclear Magnetic Resonance Verification of Synthesis: The complete proton and carbon-13 nuclear magnetic resonance spectra of H(L·Val$_1$-L·Pro$_2$-D·Ala$_3$-L·Val$_4$-Gly$_5$)$_n$-L-Val-OMe *in dimethylsulfoxide are shown in FIG. 2 where all of the resonances are assigned. The presence of peaks as required for the polymer demonstrates the correct composition and the absence of extraneous peaks demonstrates the purity of the preparation. The absence of shifted resonances for the end groups indicates that the degree of polymerization, n, is greater than about forty. By the multi-irradiation method used to achieve the assignments, even the sequence of amino acids is confirmed. Thus, the synthesis of the polymer is completely verified.*

Figure 3:
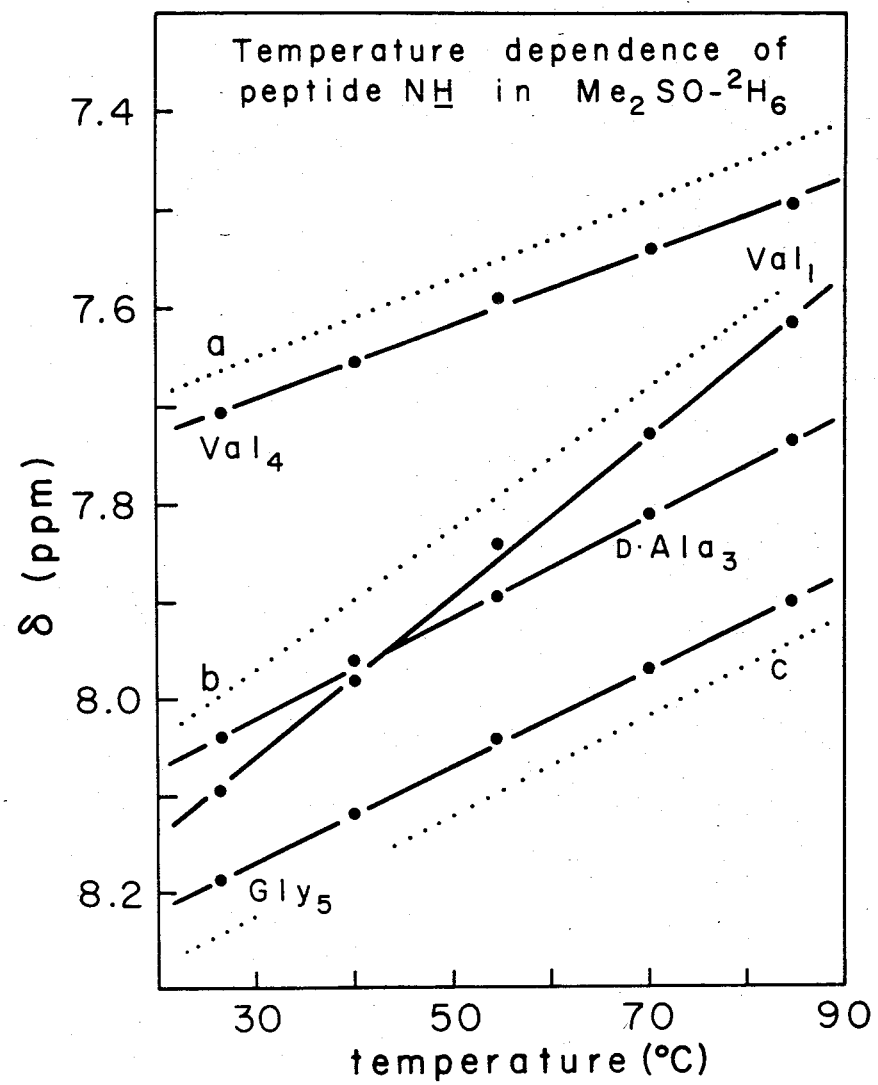
FIG. 3 shows temperature dependence in $Me_2SO$-$^2H_6$ at 100 MHz for the peptide N$\underline{H}$s of the D.Ala$_3$ polypentapeptide.

Effect of Substitution on Conformation: The temperature dependence of peptide NH chemical shift is an important means of characterizing the conformation of the elastin repeat peptides. This data is shown for D·Ala$_3$ PPP in FIG. 3 (solid curves) which is to be compared with data for the PPP of elastin (dotted curves). The sensitivity of this type of data to conformation has been well-established. This is particularly evident when comparing data on the series of molecules cyclo(VPGVG), cyclo(VPGVG)$_2$, cyclo(VPGVG)$_3$ and (VPGVG)$_n$. While the sequences of these molecules are the same, the chemical shifts and the solvent and temperature dependence of peptide NH chemical shifts are very different for each of the cyclic molecules which can only be the result of very different conformations. On the other hand, the patterns of chemical shift and temperature dependence of peptide NH resonances of the cyclopentadecapeptide and the linear high polymer, PPP, are essentially identical indicating that the cyclic molecule with n=3 is the cyclic conformational correlate of the linear PPP. In FIG. 3, the upfield position of the Val$_4$NH resonance and its low temperature dependence of chemical shift are indicative of the Pro$_2$-Gly$_3$ Type II β-turn in D·Ala$_3$ PPP as in PPP. The steeper slope for the Val$_1$NH resonance is the result of greater exposure of this moiety to the solvent. While the D·Ala$_3$ NH is upfield from the Gly$_3$ NH of PPP, this is due to the inductive effect of the β-methyl moiety. Even so, both the Gly$_5$ NH and the D-$^{Ala}$$_3$ NH of D·Ala$_3$ PPP have the same temperature dependence which is similar to that of the overlapping Gly$_5$ NH resonances (curve c) of the PPP. These shieldings are due to the presence of additional secondary structure in the dimethyl sulfoxide solvent. Thus, with the obvious shift of the D·Ala$_3$ NH resonance which is due to the change in amino acid, the patterns are very similar for (VPA'VG)$_n$ and (VPGVG)$_n$ indicating similar conformations and in particular the presence of the β-turn.

As shown in Table I, the solvent dependence of peptide C—O chemical shifts are also very similar. In column 1 for water the chemical shifts for the Val$_1$, Pro$_2$, Val$_4$ and Gly$_5$ C—O resonances are essentially identical given the ±0.05 ppm digital resolution. Since these chemical shifts are also sensitive to conformation with shifts of the order of 1.0 ppm occurring due to changes in conformation, this also indicates the same conformation for D·Ala$_3$ PPP and PPP in water. In dimethyl sulfoxide the differences in these chemical shifts are no greater than 0.15 ppm. The magnitudes of the chemical shifts on going from one solvent, $^2$H$_2$O, to the other, Me$_2$SO-[$^2$H$_6$], are indicative of the degree of exposure of the carbonyl moiety to the solvent. The least shifted is the most shielded as occurs on intramolecular hydrogen bonding. The differences plotted with respect to the Val$_1$C—O of the PPP, i.e., the β-turn carbonyl, are given in the last column of Table I. The −0.25 ppm value for the Val$_1$ C—O of the D·Ala$_3$ PPP indicates greater shielding of this Val$_1$ C—O and that the β-turn is stabilized in the D·Ala$_3$ PPP as had been anticipated from even a qualitative knowledge of the energetics of the β-turn. This is apparent in FIG. 1A where it is the radial α-hydrogen of the Gly$_3$ residue that is replaced by a methyl in D·Ala$_3$ PPP. Thus, it is established that the β-turn is not only retained in the D·Ala$_3$ analog but it is actually stabilized.

Figure 4:
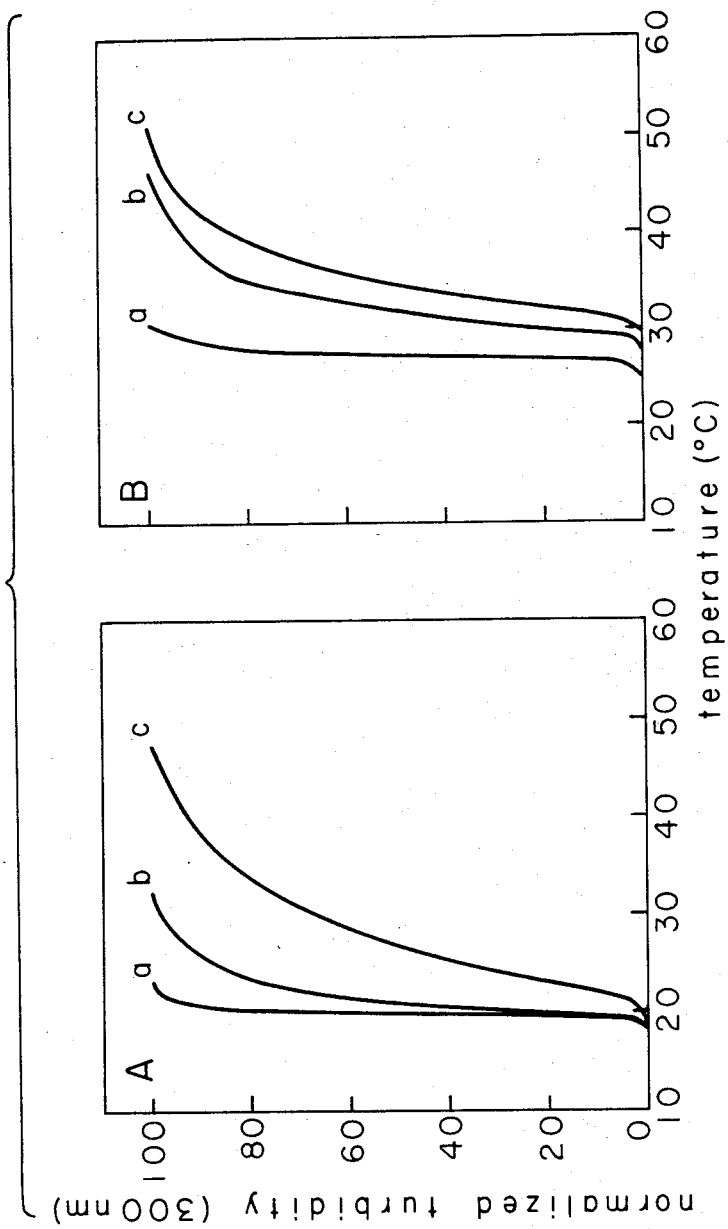
FIG. 4 shows temperature profiles of turbidity formation for the D.Ala$_3$ polypentapeptide (A) and Gly$_3$ polypentapeptide (B)

Effect of Substitution on Coacervation Properties: Tropoelastin (the precursor protein of fibrous elastin), α-elastin (a 70,000 dalton fragmentation product from fibrous elastin) and the polypentapeptide of elastin are all soluble in water in temperatures below 20° C. but on raising the temperature to the physiological range their solutions become cloudy and on standing separate into two phases. The more dense phase is viscoelastic and is referred to as the coacervate. The upper phase is called the equilibrium solution. This process of coacervation is considered to be a process of fiber formation. The coacervate, when formed by settling however, is not anisotropic because the suspended small aggregates, while comprised of parallel aligned filaments, do not align in the settling process. The temperature dependence of coacervation for D-Ala$_3$ PPP and PPP is compared in FIG. 4 where the D-Ala$_3$ PPP analog is seen to have a temperature profile for coacervation that is shifted 5° to 10° C. to lower temperatures. This is consistent with the process being an inverse temperature transition in which the dominant intermolecular forces are hydrophobic and in which the D-Ala$_3$ analog is slightly more hydrophobic.

Figure 5B:
FIG. 5 shows a scanning electron micrograph of the D.Ala$_3$ polypentapeptide coacervate at 500X.
Figure 5A:
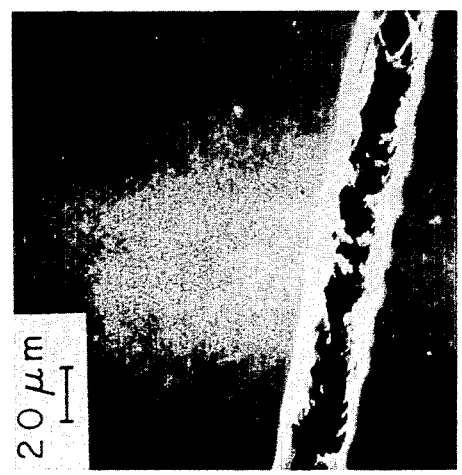

Characterization of the coacervate by scanning electron microscopy is also informative. As shown in FIG. 5A, the D-Ala$_3$ PPP coacervate forms a smooth structureless layer on a Plexiglass substrate. In FIG. 5A the coacervate was scored by a needle to demonstrate its presence. Occasionally small cracks are observed as indicated in FIG. 5B. This is in contrast to the similarly treated coacervate of α-elastin which forms large cracks on drying. The polypentapeptide coacervate is also characterized by the formation of many cracks during the drying for coating and observation in the electron microscope.

Figure 6:
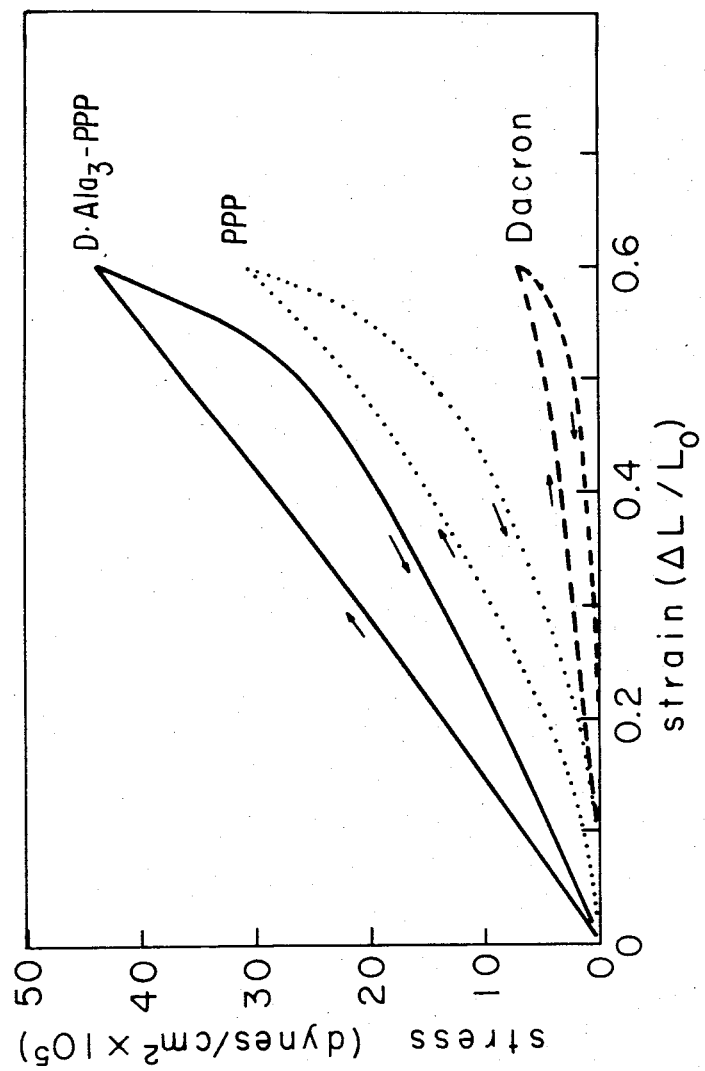
FIG. 6 shows stress-stain curves of the D.Ala$_3$ polypentapeptide compounded to Dacron with 30 Mrads of gamma irradiation along with corresponding curves for the Gly$_3$ polypentapeptide compounded to Dacron and for Dacron alone.

Effect of Substitution on Elastic Modulus: The stress-strain curve for D-Ala$_3$ PPP cross-linked and compounded to Dacron, as previously done for the PPP and disclosed in Urry et al, Biomater. Med. Dev. Art. Org., 9(3), 181 (1981), is shown in FIG. 6. For comparison the curves for similarly treated PPP and for Dacron are also included. Adequate cross-linking by γ-irradiation can be achieved with 30 Mrad for D-Ala$_3$ PPP whereas 40-60 Mrad was required for the PPP. The elastic (Young's) modulus is about $10 \times 10^6$ dynes/cm$^2$ for D-Ala$_3$ PPP-Dacron, increased from $6 \times 10^6$ dynes/cm$^2$ for PPP-Dacron. On subtracting the apparent elastic modulus obtained for the Dacron weave alone, these studies indicate that a doubling of the elastic modulus can be achieved by the D-Ala$_3$ analog.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. An elastomeric material, comprising:
an elastomeric polypeptide, wherein said polypeptide comprises pentapeptide repeating units consisting of a first amino carboxylic acid residue, a second amino carboxylic acid residue, a third amino carboxylic acid residue, a fourth amino carboxylic acid residue and a fifth amino carboxylic acid residue, wherein said repeating units comprise amino carboxylic acid residues selected from the group consisting of hydrophobic amino carboxylic acid and glycine residues wherein said residues are amino carboxylic acids which are missing a hydrogen of an amino group and a hydroxyl of a carboxyl group, wherein the third amino carboxylic acid residue of at least one repeating unit of said polypeptide has a D configuration if the first, second, fourth and fifth hydrophobic amino carboxylic acid residues which are not glycine residues have the L configuration or the L configuration if the first, second, fourth and fifth hydrophobic amino carboxylic acid residues which are not glycine residues have the D configuration and wherein said repeating units exist in a conformation having a β-turn.

2. The elastomeric material of claim 1, wherein said hydrophobic amino carboxylic acid residues are selected from the group consisting of residues of hydrophobic α-amino carboxylic acids.

3. The elastomeric material of claim 2, wherein said hydrophobic amino carboxylic acid residues are selected from the group consisting of alanine, valine, leucine, isoleucine, proline, phenylalanine, tryptophan, and methionine residues.

4. The elastomeric material of claim 3, wherein the first amino carboxylic acid residue of said repeating unit is a residue of valine, leucine, or isoleucine.

5. The elastomeric material of claim 3, wherein the second amino carboxylic acid residue of said repeating unit is a residue of proline.

6. The elastomeric material of claim 3, wherein the third amino carboxylic acid residue of said repeating unit is a residue of a hydrophobic amino carboxylic acid having no more than 10 carbon atoms in the side chain of said residue.

7. The elastomeric material of claim 3, wherein the fourth amino carboxylic acid residue of said repeating unit is a residue of valine.

8. The elastomeric material of claim 3, wherein the fifth amino carboxylic acid residue of said repeating unit is a residue of glycine.

9. The elastomeric material of claim 1, wherein said repeating unit is L-Val-L-Pro-D-Ala-L-Val-Gly or D-Val-D-Pro-L-Ala-D-Val-Gly.

* * * * *